United States Patent [19]

Craig et al.

[11] 4,365,345
[45] Dec. 21, 1982

[54] SERVO OPERATED FLUOROSCOPIC TABLE

[75] Inventors: James R. Craig, Glenview; Steven F. Nerge, Elgin, both of Ill.

[73] Assignee: The Machlett Laboratories, Incorporated, Stamford, Conn.

[21] Appl. No.: 202,095

[22] Filed: Oct. 30, 1980

Related U.S. Application Data

[63] Continuation of Ser. No. 962,726, Nov. 21, 1978.

[51] Int. Cl.$^3$ .............................................. A61B 6/08
[52] U.S. Cl. ..................................... 378/190; 378/91; 378/196
[58] Field of Search ........................... 378/190, 196, 91

[56] References Cited

U.S. PATENT DOCUMENTS

| | | | |
|---|---|---|---|
| 2,823,316 | 2/1958 | Reynolds | 250/445 R |
| 3,281,598 | 10/1966 | Hollstein | 250/445 R |
| 3,420,997 | 1/1969 | Mueller | 250/445 R |
| 4,024,403 | 5/1977 | Bernstein | 250/445 R |

Primary Examiner—Alfred E. Smith
Assistant Examiner—T. N. Grigsby
Attorney, Agent, or Firm—John T. Meaney; Joseph D. Pannone

[57] ABSTRACT

A fluoroscopic table having a table top for supporting a patient for irradiation by X-rays generated by a source located beneath the table top, which X-rays are directed through the table top and patient to a receptor located above the patient, the receptor comprising a heavy image intensifier and spot filming device, for example, movable longitudinally and transversely of the table, and the X-ray source comprising a heavy X-ray generator and collimator which are movable as a unit longitudinally and transversely of the table for constant alignment with the receptor, the mountings for the receptor and source being separate from one another and the movements thereof being individually controlled by servo mechanisms whereby precise alignment is automatically achieved and maintained.

3 Claims, 5 Drawing Figures 4,365,345

SERVO OPERATED FLUOROSCOPIC TABLE

CROSS-REFERENCE TO RELATED CASES

This is a continuation of application Ser. No. 962,726, filed Nov. 21, 1978.

BACKGROUND OF THE INVENTION

Fluoroscopic tables are commonly used for supporting a patient in a position to be irradiated by a beam of X-rays or other selected radiation. One conventional type of X-ray apparatus for diagnostic purposes includes a table having a top upon which the patient is positioned during the diagnostic procedure, and an X-ray source which is located above the patient and which directs X-rays downwardly through the patient and table top to a bucky which is carried by the table beneath the patient. The bucky includes an X-ray film cassette or carrier that positions the plane of the film substantially parallel to the table top. Such prior art apparatus is disclosed in U.S. Pat. Nos. 3,967,126 issued on June 29, 1976 to George W. Otto, Jr.

Early versions of the fluoroscopic tilt table, prior to development of appurtenances such as image intensifiers, automatic spot film devices, and spot film cameras, to name a few, involved relatively light weight components and such stages were easily counterbalanced. The resultant required efforts to manipulate these stagings were usually less than four pounds and were easily manipulated in all directions with manual effort of the fluoroscopist.

Later developments in the field of X-ray fluoroscopy included the production of X-ray image intensifiers which replace the bucky when it is desired to obtain immediate fluoroscopic viewing of an irradiated area. The image intensifier is an electron imaging device which converts an X-ray image first to an electron image and then to a visible image. Thus, when an X-ray beam is directed through a patient, there is formed an X-ray image which is directed onto the face of the image intensifier which immediately forms a visible image which may be viewed by the doctor or technician without waiting for development of films. Filming or television reproduction of the visible images produced by the image intensifier are also possible by known techniques.

One type of prior art system utilizing an X-ray image intensifier is disclosed in U.S. Pat. No. 3,912,936, issued Oct. 14, 1975 to Cunninghame et al.

Current designs of fluoroscopic tables must be capable of supporting X-ray source assemblies (generators and collimators) weighing as much as or more than about 150 pounds and receptor assemblies (image intensifiers, spot film cameras, optics) weighing as much as or more than about 250 pounds. Such current designs of fluoroscopic carriages or stagings are of massive and heavy construction in order to maintain proper alignment of components in all positions of the table. This results in the need for a large increase in manual effort to pan the assemblies over a patient due to increases in both inertia and friction.

Numerous power drives or assists have been designed to minimize the effort required by a fluoroscopist to perform the adjustment of the apparatus. Current designs include a "C" shaped carriage the upper arm of which supports the receptor assembly, with the lower arm supporting the X-ray source assembly. The carriage is adjustable longitudinally of the table to move the receptor and source assemblies as a unit, and each assembly is individually movable on its respective carriage arm in a direction transversely of the table. However, such structures possess the problems mentioned hereinabove, in addition to being costly to manufacture and expensive to maintain in terms of bearing wear, etc.

SUMMARY OF THE INVENTION

The present invention overcomes the above and other problems associated with known fluoroscopic tables by the provision of a construction which mechanically isolates the source and receptor assemblies, eliminates the bulky "C" carriage, reduces effort involved in making adjustments of the assemblies, and reduces mass and, consequently, costs.

In accordance with this invention, the source assembly is located on an individual carriage which is motor driven transversely and/or longitudinally of the table. Coupled to the source assembly is a potentiometer which is bridged with a potentiometer connected to and driven by transverse and/or longitudinal motion of the receptor assembly. When the receptor assembly is manually moved, precise alignment of the source assembly with the receptor assembly is maintained by a servo amplifier system which is arranged to drive the source assembly motor to keep both potentiometers at the same resistance.

BRIEF DESCRIPTION OF THE DRAWINGS

The above and other advantages of this invention will become apparent from the following description taken in connection with the accompanying drawings, wherein.

DESCRIPTION OF THE PREFERRED EMBODIMENTS

Figure 1:
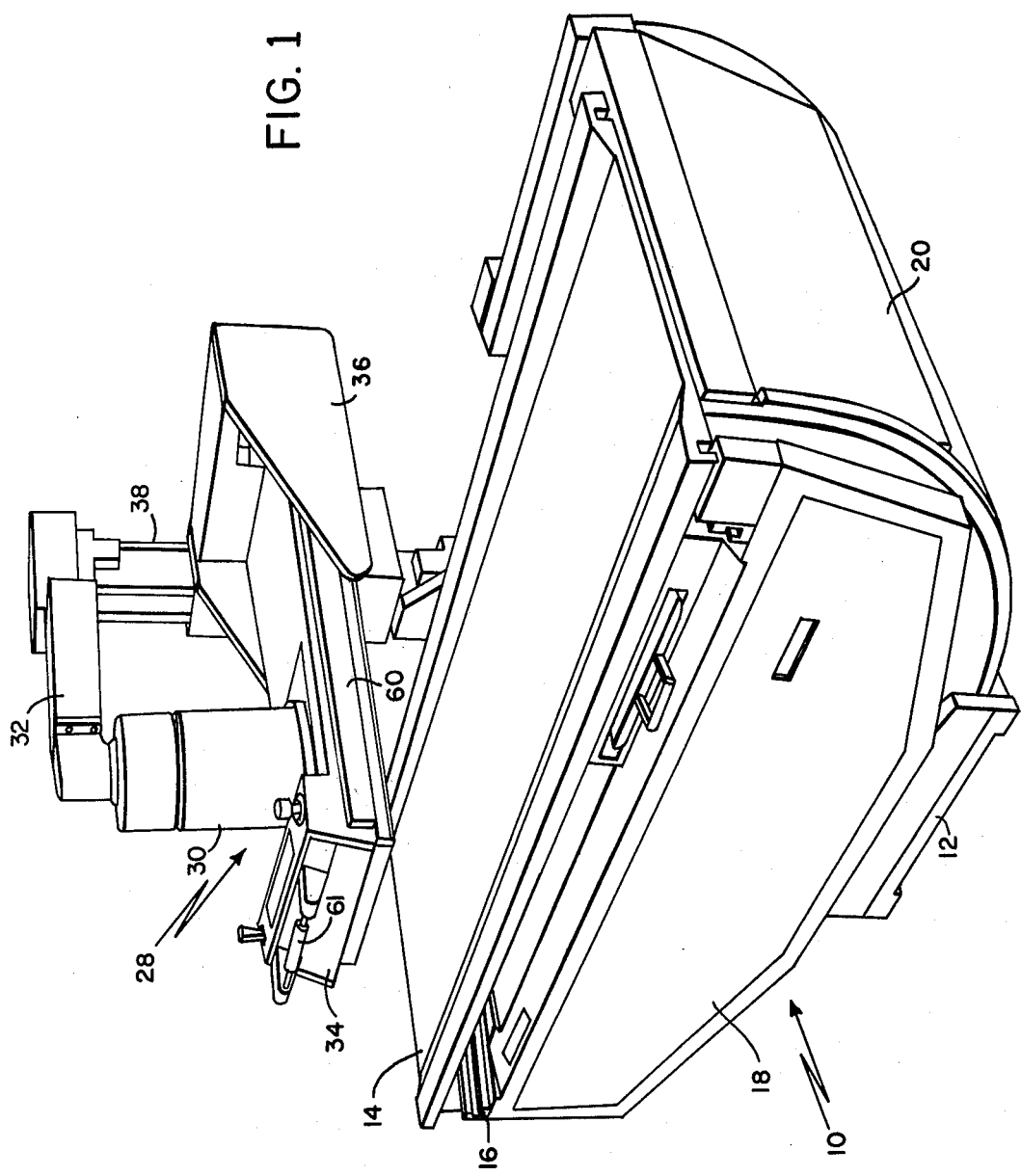
FIG. 1 is an isometric view of a fluoroscopic table embodying the invention.

Referring more particularly to the drawings, wherein like characters of reference designate like parts throughout the several views, there is shown in FIG. 1 a fluoroscopic table 10 mounted on a base or pedestal 12 and having a top 14 on which a patient lies. The top 14 is suitably mounted on a frame or carriage 16 for planar movement in any direction, the means for accomplishing such movement not comprising a part of this invention. The table has a front panel 18 and end panels 20 which enclose the operative mechanisms within the structure.

Figure 2:
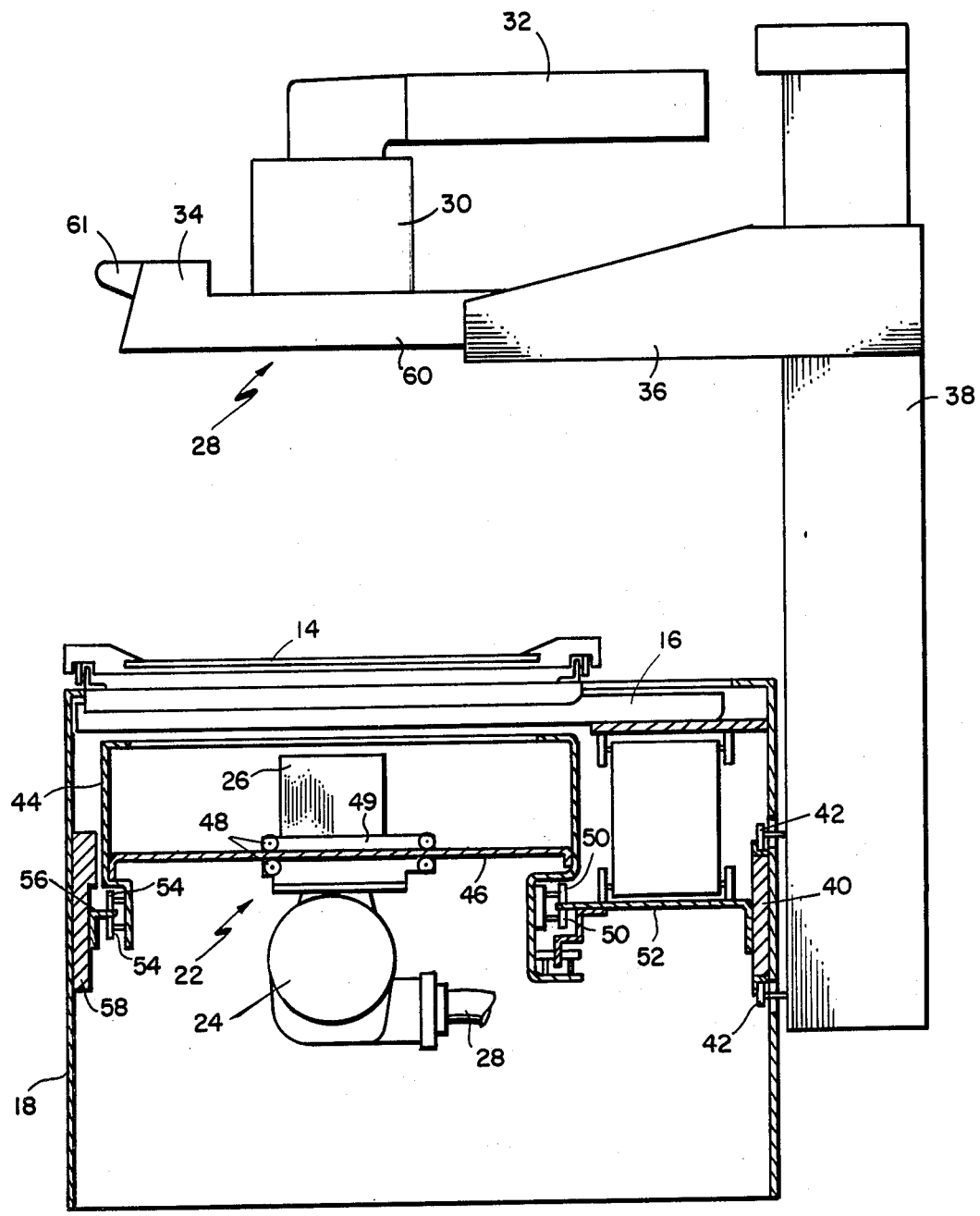
FIG. 2 is a vertical sectional view taken substantially on line 2—2 of FIG. 1 looking in the direction of the arrows.

As seen in FIG. 2, a radiation source assembly 22 is located within the table and includes an X-ray generator 24 and an X-ray collimator 26.

The X-ray tube or generator 24 is connected by cables 28 to a suitable power source and is adapted to generate X-radiation which passes upwardly through the collimator 26 and through the table top 14 to a patient lying on the top. The X-ray beam passing through the patient will fall onto an X-ray image intensifier 30 which, together with additional equipment such as optical devices 32 and spot film devices 34, is mounted by a suitable support 36 at the upper end of a tower 38. Tower 38 extends vertically from the rear of the table as shown in FIG. 2, and the receptor assembly 28 is vertically movable on the tower 38 toward and away from the source assembly 22 as will be described.

The lower end of the tower is movably mounted on the rear of the table and, as shown in FIG. 2, is secured to a longitudinally extending frame member 41. The tower and receptor assembly thereon are adapted to move as an independent unit longitudinally of the table on frame member 41 as by upper and lower rollers 42, thus positioning the receptor assembly thereon in desired position with respect to the patient.

The receptor assembly 28 is independently manually movable laterally or transversely of the table in support 36 by suitable conventional slide mechanism 60, and such transverse adjustment, as well as longitudinal adjustment may be accomplished by manual manipulation on the part of the operator through the use of a handle 61.

The source assembly is positioned within a rigid frame 44 and a pair of transversely extending plates 46 serve as tracks engaged by rollers 48 carried by a support collar 49 or the like which is secured about the collimator 26. Thus, the source assembly is independently movable on the tracks 48 in a direction laterally or transversely of the table.

To permit independent longitudinal movement of the source assembly 22, the frame 44 is mounted as by rollers 50, at the back side of the structure, which engage a longitudinally extending plate 52 fixed to frame member 41. At the front of the structure, rollers 54 on the frame 44 engage a track or angle bar 56 which extends longitudinally of the table on table frame member 58. Thus, the source assembly 22 may be independently moved longitudinally of the table. The source and receptor assemblies 22 and 28 are maintained in vertical alignment at all longitudinal and lateral positions of the assemblies as will be described.

The receptor assembly 28 is fixed to the tower 38 as described and may be adjusted transversely or longitudinally of the table by manual manipulation on the part of the operator as described. The source assembly 22 must also be simultaneously transversely or longitudinally adjusted in order to constantly maintain the two assemblies in aligned relations. In order to achieve simultaneous and corresponding movement of the source assembly 22 with the manual adjustment of the receptor assembly 28, there is provided a servo system whereby when the receptor assembly 28 is manually moved the servo system will operate to cause simultaneous corresponding movement of the source assembly 22.

Figure 3:
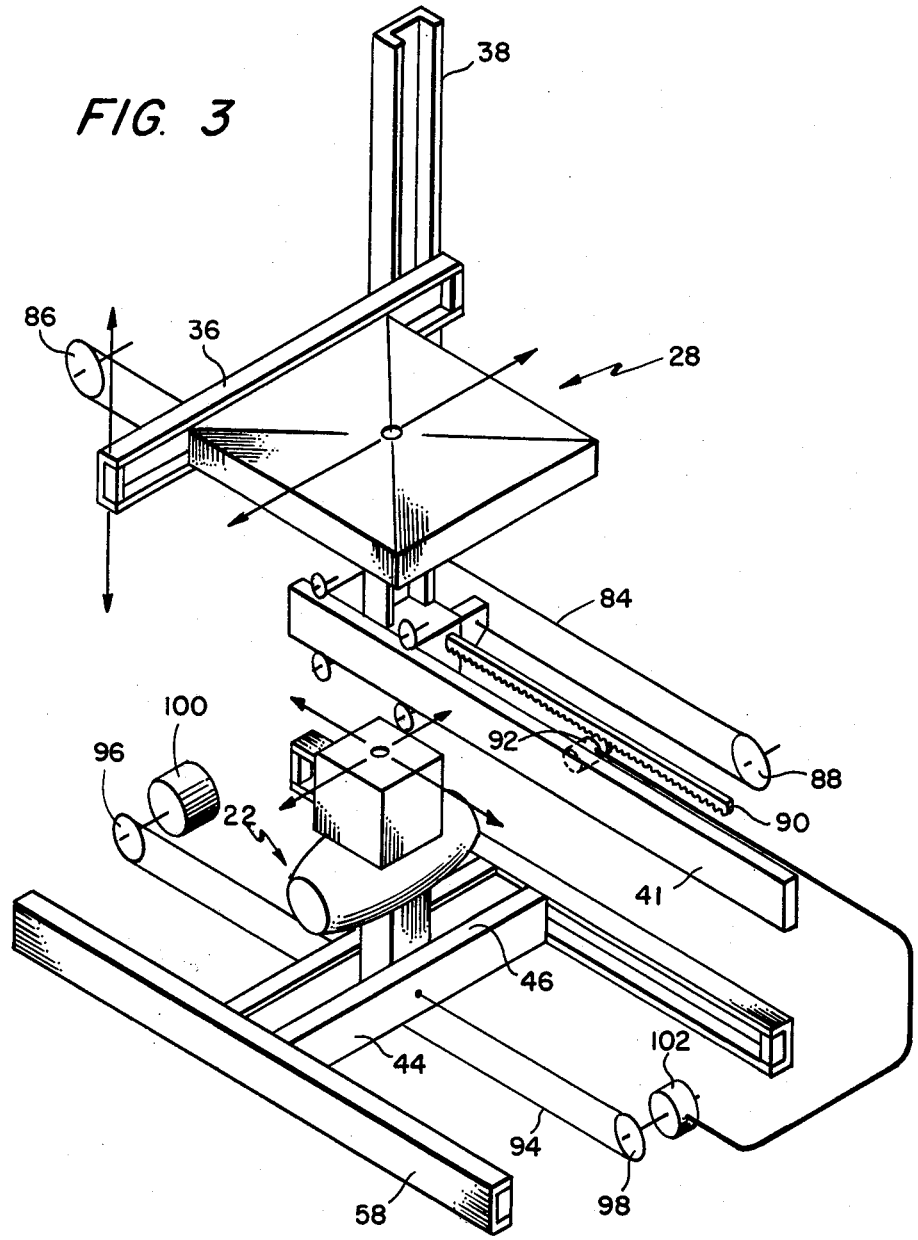
FIG. 3 is a view illustrating diagrammatically the longitudinal adjustments of the receptor and source assemblies.

A better understanding of the various adjustments achieved by the described structures may be had from the diagram in FIG. 3. Here it will be seen that the receptor assembly shown diagrammatically at 28 is itself manually adjustable transversely of the table by sliding the assembly 28 in support 36 which is mounted for separate vertical adjustment on tower 38.

The source assembly 22 is movable transversely of the table by sliding the assembly along the tracks 46 of frame 44, which frame 44 is supported at the front and rear of the table on frame members 58 and 40 respectively.

Figure 4:
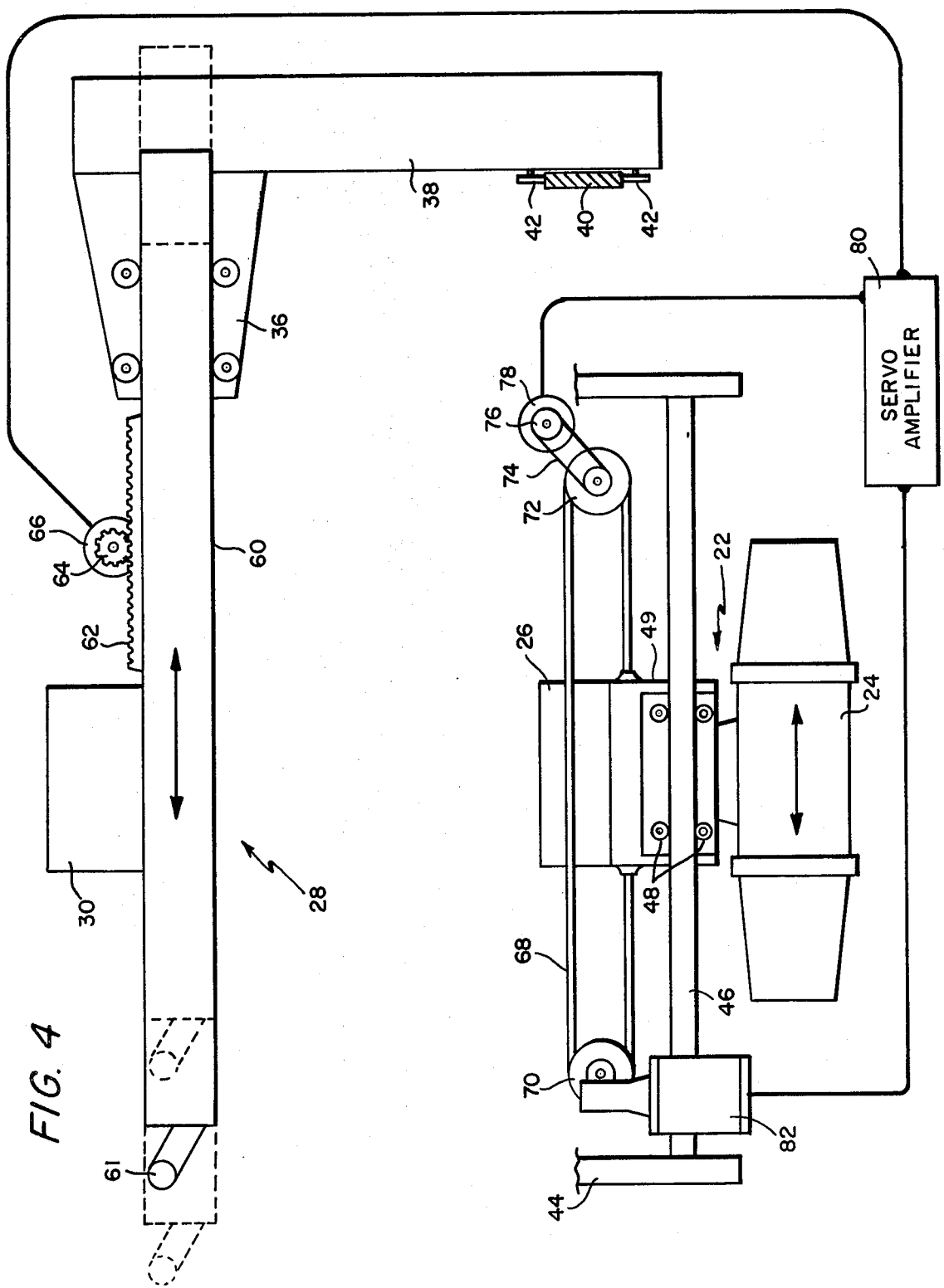
FIG. 4 is a view illustrating diagrammatically the transverse adjustments of the receptor and source assemblies.

In order to provide automatic and simultaneous movement of the source assembly 22 when the receptor assembly 28 moves transversely of the table, a servo system is employed as shown diagrammatically in FIG. 4. The operator will, by grasping handle 61, move the receptor assembly 28 in a direction toward or away from the tower 38, the receptor slide bar 60 sliding reciprocally in support 36. Slide bar 60 carries a toothed rack 62 which meshes with a toothed gear or pinion 64 on a potentiometer 66 which is fixed to the tower in any suitable manner. Thus, when the receptor assembly 28 is moved transversely of the table it will, through rack 62 and pinion 64 cause adjustment of the resistance in the potentiometer 66.

The source assembly 22 is movable transversely of the table on tracks 46 by a chain, belt or cable 68 which is wound over a pair of pulleys 70 and 72 suitably supported on the front and rear of the table. The ends of cable 68 are secured directly to opposite sides of the support collar 49 and thereby moves the source assembly when the pulleys 70 and 72 rotate. A cable or belt 74 is mounted over pulley 72 and over a pulley 76 on a sensing potentiometer 78 which is fixed to the base. Potentiometer 78 is electrically connected to a servo amplifier 80 which is also connected to a servo motor 82 suitably mounted on the frame 44. The motor 82 is operatively connected to pulley 70 for driving same and thereby moving cable 68 to adjust the source assembly 22 transversely.

Figure 5:
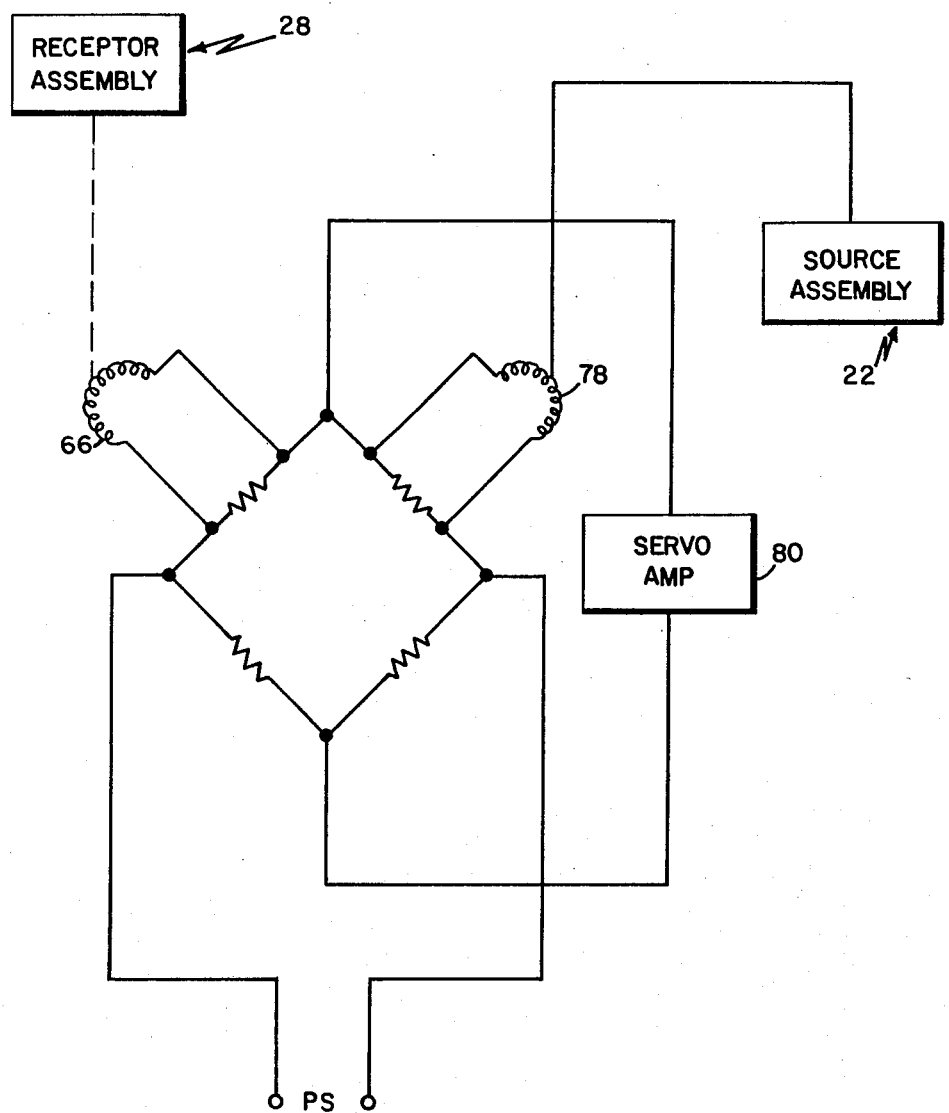
FIG. 5 is a schematic diagram of the servo circuit utilized in performing the receptor and source assembly adjustments.

The potentiometer 78 senses the position of the source assembly 22 and its resistance represents that position. The potentiometer 66 on the receptor assembly 28 is also connected to the servo amplifier 80. Thus, when the receptor assembly 28 is moved, the resultant differences in the resistances in the two potentiometers 66 and 78 are sensed and as a result the servo motor 82 is operated to move the source assembly to the extent where the resistance in potentiometer 78 again matches the resistance in potentiometer 66, which indicates that the two assemblies are transversely aligned. The circuit in FIG. 5 illustrates these functions.

Referring again to FIG. 3, there is illustrated diagrammatically the longitudinal adjustments of the receptor and source assemblies. Receptor assembly 28 is moved longitudinally of the table, this being done manually by the operator by means of handle 61. Since the receptor assembly 28 is mounted on tower 38, such transverse movement of the receptor assembly causes corresponding movement of the tower along frame member 40, as described hereinbefore.

A cable 84 is wound over pulleys 86 and 88 and has its ends connected to respective opposite sides of the tower 38. Tower 38 carries a toothed rack 90 which meshes constantly with a gear on a potentiometer 92 fixed to the frame member 41. Thus, when the receptor assembly 28 is moved longitudinally of the table, consequent movement of the tower 38 and rack 90 will cause a change in resistance of the potentiometer 92.

From FIG. 3 it will be seen that the source assembly 22 is individually movable longitudinally of the table. The frame 44 is longitudinally movable on frame members 58 and 40 under control of a cable 94 which is wound over spaced pulleys 96 and 98 and has its ends connected to opposite ends of the frame 44. One pulley 96 is connected to a motor 100 whereby the source assembly may be longitudinally moved. The second pulley 98 is operatively connected to a potentiometer 102 which senses the position of the source assembly and produces a resistance accordingly.

The two potentiometers 92 and 102 are interconnected in a manner similar to that shown in FIG. 5. Therefore, when the resistance in potentiometer 102 is different from the resistance in potentiometer 92, the motor 100 will move the source assembly to the extent necessary to produce a resistance in potentiometer 102 equal to the resistance in potentiometer 92. When this occurs, the receptor and source assemblies are aligned and the motor 100 stops.

It is to be understood that the described servo mechanisms may be utilized with the longitudinal adjustments of the receptor and source assemblies, the transverse adjustments, or both.

From the foregoing it will be apparent that various modifications and changes in the structures shown and described and in their operation may be made by those skilled in the art without departing from the spirit of the invention as expressed in the accompanying claims. Therefore all matter shown and described is to be interpreted as illustrative and not in a limiting sense.

What is claimed is:

1. A fluoroscopic apparatus comprising:
   a fluoroscopic table having a base and a patient-supporting surface
   a radiation source means within the base and disposed for directing through said surface a beam of radiation having a central axis substantially normal to said surface;
   a fluoroscopic receptor means spaced from the base and disposed for receiving said beam when aligned with the source means and producing corresponding fluoroscopic images, said receptor means being movable translationally along said patient supporting surface;
   source support means for supporting the source means independent of the receptor means and translationally movable with respect to said patient-supporting surface while maintaining said beam substantially normal to said surface;
   and servo means connected to the source means and the receptor means for automatically maintaining the source means translationally in registrational alignment with the receptor means while maintaining said axis of said beam substantially normal to said surface to produce a sequence of fluoroscopic images.

2. A fluoroscopic apparatus comprising:
   a fluoroscopic table having a base and a patient-supporting surface disposed for fluoroscopic examination of a patient;
   a radiation source means disposed within the base for generating a beam of X-rays having a central axis substantially normal to said surface and for directing said x-ray beam through said patient;
   a fluoroscopic receptor means spaced from the base for receiving said X-ray beam directed through the patient when aligned with the source means and supported for individual scanning translational movement with respect to at least a major portion of said patient;
   source support means disposed in said base for supporting the source means independently of the receptor means and translationally movable with respect to said portion of said patient while maintaining said axis of the beam substantially normal to said surface; and
   servo means for automatically moving the source means translationally into registrational alignment with said scanning receptor means to produce a sequential series of fluoroscopic images corresponding to said scanned portion of the patient while maintaining said axis of the beam substantially normal to said surface.

3. A fluoroscopic apparatus comprising:
   a fluoroscopic table having a base and a patient-supporting surface disposed for fluoroscopic scanning examination of a patient;
   a radiation source assembly mounted in said base and disposed to generate an X-ray beam having a central axis substantially normal to said surface and to direct said beam through said surface;
   source support means disposed in said base and supportingly coupled to the source assembly for permitting translational scanning movement of the source assembly along said patient while maintaining said central axis of the beam substantially normal to said surface;
   a fluoroscopic receptor assembly spaced from said base and disposed for receiving said x-ray beam when said assemblies are aligned and producing corresponding fluoroscopic images;
   receptor support means disposed for supporting the receptor assembly independently of the source assembly and for permitting translational scanning movement with respect to said patient;
   means for moving the receptor assembly translationally to scan said patient and for producing a corresponding electrical control signal in accordance with the scanning movement; and
   servo means responsive to the electrical control signal for automatically moving the source assembly translationally in registrational alignment with the receptor assembly to produce a corresponding scanning of the beam of radiation along the patient while maintaining said beam substantially normal to said surface.

* * * * *